United States Patent [19]

Eicken et al.

[11] Patent Number: 4,494,983
[45] Date of Patent: Jan. 22, 1985

[54] CHLOROACETIC ACID CYCLOHEXYLAMIDES, THEIR PREPARATION, THEIR USE FOR CONTROLLING WEEDS AND AGENTS FOR THIS USE

[75] Inventors: Karl Eicken, Wachenheim; Norbert Goetz, Worms; Bruno Wuerzer, Otterstadt, all of Fed. Rep. of Germany

[73] Assignee: BASF Aktiengesellschaft, Fed. Rep. of Germany

[21] Appl. No.: 383,977

[22] Filed: Jun. 1, 1982

[30] Foreign Application Priority Data

Jun. 15, 1981 [DE] Fed. Rep. of Germany ....... 3123731

[51] Int. Cl.³ .................... A01N 37/26; A01N 43/64; C07C 103/38; C07D 249/08
[52] U.S. Cl. .......................... 71/118; 71/88; 71/90; 71/92; 548/262; 548/378; 549/373; 549/426; 549/454; 549/495; 564/210; 564/248; 564/462
[58] Field of Search .......................... 564/210; 71/118

[56] References Cited

U.S. PATENT DOCUMENTS

| 3,007,786 | 11/1961 | Hamm et al. | 564/210 |
| 3,141,758 | 7/1964 | Hamm et al. | 564/210 |
| 3,356,724 | 12/1967 | Olin | 260/561 |
| 4,021,224 | 5/1977 | Pallos et al. | 564/210 |
| 4,155,744 | 5/1979 | Alt | 71/88 |
| 4,258,196 | 3/1981 | Chupp et al. | 564/210 |
| 4,311,858 | 1/1982 | Chupp | 564/210 |
| 4,322,553 | 3/1982 | Chupp | 564/210 |

FOREIGN PATENT DOCUMENTS 532981 8/1957 Belgium .

Primary Examiner—Alton D. Rollins
Attorney, Agent, or Firm—Keil & Weinkauf

[57] ABSTRACT

Novel chloroacetic acid cyclohexylamides of the formula I

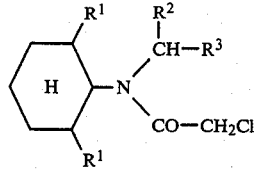

where $R^1$, $R^2$ and $R^3$ have the meanings given in the description, their preparation and their use as herbicides.

8 Claims, No Drawings

CHLOROACETIC ACID CYCLOHEXYLAMIDES, THEIR PREPARATION, THEIR USE FOR CONTROLLING WEEDS AND AGENTS FOR THIS USE

The present invention relates to chloroacetic acid cycloalkylamides, processes for their preparation, herbicides containing the compounds and methods of controlling undesirable plant growth using the compounds.

Belgian Pat. No. 532,981 disclosed chloroacetic acid cycloalkylamides, e.g. chloroacetic acid N-allyl-N-cyclohexylamide, as herbicides some time ago.

We have found that chloroacetic acid cyclohexylamides of the formula I

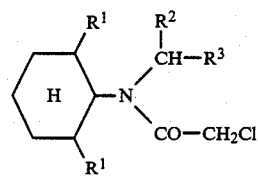

where $R^1$ is methyl or ethyl, $R^2$ is hydrogen or $C_1$–$C_3$-alkyl and $R^3$ is $C_1$–$C_6$-alkyl which is unsubstituted or substituted by $C_1$–$C_4$-alkoxy or $C_1$–$C_4$-alkoxycarbonyl, or is $C_2$–$C_3$-alkenyl, $C_2$–$C_3$-alkynyl, furanyl or tetrahydrofuranyl, or is phenyl which is unsubstituted or substituted by halogen, or is (bis-$C_1$–$C_6$-alkoxy)-methyl, or is dioxanyl or dioxolanyl which is unsubstituted or substituted by $C_1$–$C_3$-alkyl, and, if $R^2$ is hydrogen, may also be $C_1$–$C_8$-alkoxy, $C_3$–$C_6$-alkenyloxy, $C_3$–$C_6$-alkynyloxy, $C_3$–$C_6$-cycloalkylmethoxy, $C_4$–$C_6$-cycloalkoxy, $C_1$–$C_6$-alkoxyethoxy, tetrahydrofuranylmethoxy, tetrahydropyranylmethoxy or azol-1-yl, have substantially improved herbicidal properties and at the same time are still well tolerated by crops.

For the purposes of the invention, examples of alkyl and of the alkyl moiety in alkoxy or alkoxycarbonyl in $R^2$ and $R^3$ are, depending on the stated number of carbon atoms, methyl, ethyl, n-propyl, iso-propyl, n-, iso-, sec.- or tert.-butyl, pentyl and hexyl, and isomers thereof.

For the purposes of the invention, alkenyl may, depending on the stated number of carbon atoms in $R^3$, be in particular vinyl, 1-methylvin-1-yl, 2-methyl-vin-1-yl or allyl, and alkynyl may be ethynyl or prop-1-yn-1-yl.

Suitable cycloalkyl radicals in a cycloalkoxy or cycloalkylmethoxy group are, depending on the stated number of carbon atoms, cyclopropyl, cyclobutyl, cyclopentyl and cyclohexyl.

For the purposes of the invention, dioxanyl may in particular be 1,3-dioxan-1-yl, which can be substituted in the 4- and/or 5-position by methyl, ethyl or propyl. Azol-1-yl is pyrazol-1-yl or 1,2,4-triazol-1-yl.

In the compounds of the formula I, the substituents $R^1$ can be in the cis-, trans- or cis/trans-position relative to the nitrogen, and the compounds can therefore be in the sterically pure form or in the form of isomer mixtures.

The compounds of the formula I can be prepared by (a) reacting an N-substituted cyclohexylamine of the formula II

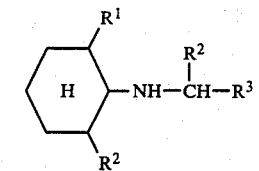

where $R^1$, $R^2$ and $R^3$ have the above meanings, with chloroacetic anhydride or a chloroacetyl halide, or (b) if $R^2$ is hydrogen and $R^3$ is $C_1$–$C_8$-alkoxy, $C_3$–$C_6$-alkenyloxy, $C_3$–$C_6$-alkynyloxy, $C_3$–$C_6$-cycloalkylmethoxy, $C_4$–$C_6$-cycloalkoxy, $C_1$–$C_6$-alkoxyethoxy, tetrahydrofuranylmethoxy, tetrahydropyranylmethoxy or azol-1-yl, reacting a chloroacetic acid N-chloromethyl-N-cyclohexylamide of the formula III

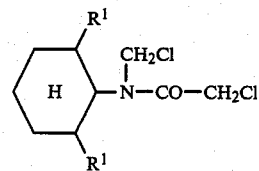

where $R^1$ has the above meanings, with a compound of the formula $R^3H$, where $R^3$ has the meanings given above under (b).

In process (a), a compound II is reacted with chloroacetic anhydride or, preferably, chloroacetyl chloride, preferably in a solvent which is inert toward the reactants, to give a chloroacetic acid cyclohexylamide according to the invention. An organic or inorganic base, such as a trialkylamine, pyridine, bicarbonate, carbonate or alkali metal hydroxide, can be used in the reaction, and preferred suitable diluents are water-immiscible solvents, such as halohydrocarbons, e.g. methylene chloride, chloroform and chlorobenzene, and hydrocarbons, e.g. cyclohexane, heptane, toluene and xylene. The stoichiometric amount of chloroacetyl chloride and not less than the stoichiometric amount of the base, based on the N-substituted cyclohexylamine of the formula II employed, is used. The reactions with chloroacetyl chloride are carried out at from $-20°$ to $+150°$ C., preferably at from $0°$ to $110°$ C.

The starting compounds of the formula II can be prepared by reacting a cyclohexylamine of the formula

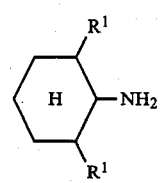

where $R^1$ has the above meanings, with an alkylating agent of the formula

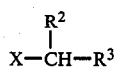

where $R^2$ and $R^3$ have the above meanings and X is a leaving group, e.g. chloride, bromide, iodide, p-toluenesulfonate, benzenesulfonate or trifluoroacetate. The alkylation reaction can be carried out in the absence of a solvent, depending on the type and reactivity of the alkylating agent. Suitable diluents are aprotic dipolar solvents, such as nitriles, e.g. acetonitrile, and amides, e.g. dimethylformamide, and protic solvents, such as alcohols e.g. ethanol and isopropanol, and water, and mixtures of these solvents. Inorganic bases, e.g. carbonates, bicarbonate, alkali metal hydroxides and organic bases such as trialkylamines, as well as the cyclohexylamine of the formula II used as the reactant, can be used as acid acceptors for the HX formed, e.g. hydrogen chloride or hydrogen bromide. Advantageously, not less than 1 mole of cyclohexylamine of the formula II and not less than 1 mole of inorganic or organic base are used per mole of alkylating agent of the formula III. The reaction is carried out at from 25° to 150° C. The N-substituted cyclohexylamine of the formula IV is usually isolated by fractional distillation, where appropriate after being released from its salt and where appropriate after water-miscible solvents have been removed.

Some of the N-substituted cyclohexylamides of the formula II where $R^3$ is not linked to the CH group via oxygen or nitrogen can also be prepared by reacting a cyclohexylamine of the formula IV with a carbonyl compound of the formula

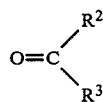
VI where $R^2$ has the above meanings and $R^3$ is not linked to the carbonyl group via oxygen or nitrogen, water being split off, and reducing the resulting Schiff base with catalytically activated hydrogen or a hydrogen donor, such as a complex hydride, e.g. $NaBH_4$ or $LiAlH_4$, to an N-substituted cyclohexylamine of the formula II and reacting this with chloroacetyl chloride as described above.

The water of reaction formed during preparation of the Schiff base is advantageously removed by azeotropic distillation with a conventional entraining agent, e.g. a hydrocarbon, such as n-pentane, n-hexane, cyclohexane, benzene, toluene, xylene, methylene chloride or chloroform.

The hydrogenation of the Schiff base is carried out on a catalyst such as a noble metal catalyst, e.g. palladium or platinum on a suitable support, or Raney nickel at from 20° to 200° C., preferably at from 50° to 150° C., under a hydrogen pressure of from 10 to 500 bar.

Those compounds of the formula IV which are not yet known can be prepared in sterically pure form in a particularly simple manner by hydrogenating amination of a 2,6-dialkylphenol and subsequent distillation.

Reaction (b) is carried out in the presence of an organic or inorganic base, such as a trialkylamine, pyridine, bicarbonate, alkali metal carbonate or alkali metal hydroxide, at from 20° to 120° C.

The compounds of the formula III can be obtained by reacting a cyclohexylamine of the formula II with formaldehyde to give a formimine of the formula

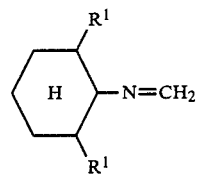
VII where $R^1$ has the above meanings, and subsequent adduct formation with chloroacetyl chloride.

The Schiff bases of the formula VII are prepared by reacting 1 mole of a cyclohexylamine of the formula IV with an aqueous solution of not less than 1 mole of formaldehyde in the presence or absence of a diluent, e.g. a hydrocarbon or halohydrocarbon, at from $-5°$ to 100° C., preferably at from 0° to 50° C. and especially at room temperature. The Schiff base is then dried and, if necessary after distillation, subjected to adduct formation with not less than 1 mole of chloroacetyl chloride at from 0° to 100° C. in the presence or absence of a diluent which is inert towards the reactants, to give a chloroacetic acid N-chloromethyl-N-cyclohexylamide of the formula III. If stoichiometric amounts are used, this intermediate can be isolated as an oil. However, it is simpler to react the crude product with an alcohol, glycol monoether, pyrazole or 1,2,4-triazole in the reaction solution, using a base. From 1 to 10 moles, preferably from 2 to 5 moles, of alcohol or from 1 to 2 moles of pyrazole or triazole and, as an acid acceptor for the hydrogen chloride liberated, not less than 1 mole of base, preferably of tertiary amine, e.g. triethylamine, are generally used per mole of Schiff base. This reaction step is carried out at from 0° to 100° C., preferably at room temperature. To isolate the chloroacetic acid cyclohexylamide of the formula I according to the invention, excess alcohol or azole and the amine hydrochloride formed are removed by washing with water, the reaction mixture is dried, the solvent is evaporated off and the crude product is further purified, if necessary, by distillation or recrystallization.

In the Examples which follow and which illustrate the various possible ways of preparing the chloroacetic acid cyclohexylamides according to the invention, parts by weight bear the same relation to parts by volume as that of the kilogram to the liter.

EXAMPLE 1

(a) Preparation of the starting material 1,650 parts by weight of 2,6-dimethylphenol and 150 parts by weight of a pulverulent catalyst containing 10.0% by weight of palladium and 5.0% by weight of praseodymium oxide on aluminum oxide were introduced into a stirred autoclave having a capacity of 10,000 parts by volume. The autoclave was closed and 1,370 parts by weight of ammonia were forced in. The autoclave was then heated to 250° C. and hydrogen was introduced to bring the pressure to 300 bar. The autoclave was kept at the reaction temperature until constant pressure was achieved (about 10 hours). It was then allowed to cool and the mixture was filtered to give 1,691 parts by weight (98.5%) of 2,6-dimethylcyclohexylamine which, according to gas chromatography and NMR analysis, had the following isomer distribution:

56% of trans,trans-2,6-dimethylcyclohexylamine,
14% of cis,cis-2,6-dimethylcyclohexylamine and 30% of cis,trans-2,6-dimethylcyclohexylamine.

The isomers were separated by fractional distillation on a column having 45 plates. The individual isomer forms were obtained in a purity of not less than 95% at the boiling points given below:

trans,trans-2,6-dimethylcyclohexylamine at 166° C./1,012 mbar cis,cis-2,6-dimethylcyclohexamine at 168° C./1,012 mbar cis,trans-2,6-dimethylcyclohexylamine at 172° C./1,012 mbar A mixture of 29.8 parts by weight of propargyl bromide and 20 parts by volume of acetonitrile was added dropwise, at from 20° to 25° C., to a solution of 63.5 parts by weight of trans,trans-2,6-dimethylcyclohexylamine in 150 parts by volume of acetonitrile under nitrogen and with stirring, stirring was continued for 1 hour and the mixture was refluxed for 5 hours. The acetonitrile was evaporated off, the residue was partitioned between 100 parts by volume of methylene chloride and 150 parts by volume of 10% strength potassium hydroxide solution and the organic phase was separated off and extracted with three times 100 parts by volume of methylene chloride. The methylene chloride was evaporated off from the combined organic phases and the residue was subjected to fractional distillation under a reduced pressure of nitrogen to give 28.0 parts by weight of N-propargyl-trans,trans-2,6-dimethylcyclohexylamine of boiling point 93°–96° C./18 mbar ($n_D^{20}$=1.4717), and 15.0 parts by weight of first runnings of boiling point 63°–77° C./16 mbar containing 25% of the desired product.

(b) Preparation of the end product 19.4 parts by weight of chloroacetyl chloride in 20 parts by volume of toluene were added dropwise, at 0° C., to a mixture of 25.7 parts by weight of N-propargyl-trans,trans-2,6-dimethycyclohexylamine in 150 parts by volume of toluene and 81.2 parts by weight of 10% strength sodium hydroxide solution with thorough mixing, and stirring was continued for 3 hours at 20° C. The toluene phase was washed with water, dried and evaporated, and the residue was distilled to give 22.7 parts by weight of N-propargyl-N-(trans,trans-2,6-dimethylcyclohexyl)-α-chloroacetamide of boiling point 132°–134° C./0.4 mbar (melting point 59°–62° C.).

EXAMPLE 2

(a) Preparation of the starting material 52.8 parts by weight of methoxyacetone were added dropwise to a solution of 76.2 parts by weight of trans,trans-2,6-dimethylcyclohexylamine in 200 parts by volume of n-hexane in the course of 1 hour, under nitrogen and with stirring under reflux, while 10.5 parts by volume of water were removed by azeotropic distillation in the course of about 3 hours. After the n-hexane had been evaporated off, the residue was distilled under nitrogen to give 83.0 parts by weight of methoxy-isopropylidene-trans,trans-2,6-dimethylcyclohexylamine of boiling point 107°–109° C./17 mbar ($n_D^{20}$=1.4638).

29.7 parts by weight of NaBH$_4$ were introduced into a solution of 76.0 parts by weight of methoxy-isopropylidene-trans,trans-2,6-dimethylcyclohexylamine in 250 parts by volume of methanol at from 10° to 25° C. in the course of 2 hours, with stirring and ice cooling, and the mixture was refluxed for 1.5 hours. The methanol was evaporated off, the residue was partitioned between methylene chloride and water and the organic phase was distilled to give 64.0 parts by weight of N-(1-methoxy-prop-2-yl)-trans,trans-2,6-dimethylcyclohexylamine of boiling point 117°–118° C./22 mbar.

(b) Preparation of the end product

A solution of 12.4 parts by weight of chloroacetyl chloride in 20 parts by volume of toluene was added dropwise at 80° C. to a solution of 19.9 parts by weight of N-(1-methoxy-prop-2-yl)-trans,trans-2,6-dimethylcyclohexylamine in 100 parts by volume of toluene under nitrogen in the course of 15 minutes. The mixture was then refluxed for 3 hours, while nitrogen was passed through. The mixture was cooled, washed with 200 parts by volume of water, 50 parts by volume of 2N HCl, 50 parts by volume of NaHCO$_3$ solution and 50 parts by volume of water in succession and dried, and the toluene was evaporated off to give 20.5 parts by weight of N-(1-methoxy-prop-2-yl)-N-(trans,trans-2,6-dimethylcyclohexyl)-4-chloroacetamide, of melting point 120°–122° C. (methanol).

EXAMPLE 3

(a) Preparation of the starting material 110.0 parts by weight of 37% strength formalin solution were added dropwise, in the course of 30 minutes to a solution of 152.0 parts by weight of trans,trans-2,6-dimethylcyclohexylamine in 450 parts by volume of methylene chloride at from 25° to 28° C. under nitrogen and with stirring, and stirring was continued for 4 hours. The organic phase was separated off, washed with twice 100 parts by volume of water and dried. The methylene chloride was evaporated off and the residue was distilled under nitrogen to give 136.0 parts by weight of trans,trans-2,6-dimethylcyclohexylformimine of boiling point 59°–60° C./20 mbar ($n_D^{20}$=1.4634).

(b) Preparation of the end product

A solution of 152.9 parts by weight of trans,trans-2,6-dimethylcyclohexylformimine in 100 parts by volume of cyclohexane was added dropwise to a solution of 124.3 parts by weight of chloroacetyl chloride in 100 parts by volume of cyclohexane at from 20° to 25° C., with ice-cooling, stirring and exclusion of moisture, and stirring was continued for 16 hours at 25° C.

This mixture was diluted with 200 parts by volume of cyclohexane, a mixture of 184.0 parts by weight of ethanol and 112.0 parts by weight of triethylamine was added dropwise at from 20° to 25° C., with ice-cooling and stirring, and stirring was continued for 24 hours at room temperature. The mixture was washed with three times 150 parts by volume of water each time and dried, and the cyclohexane was evaporated off to give 295.0 parts by weight of an oil from which 262.0 parts by weight of N-(ethoxymethyl)-N-(trans,trans-2,6-dimethylcyclohexyl)-α-chloroacetamide of boiling point 122°–124° C./0.5 mbar ($n_D^{20}$=1.4855) were obtained by distillation under nitrogen.

The starting compounds listed in the Tables which follow can be or have been prepared by methods similar to those in Example 1(a), 2(a) or 3(a):

TABLE 1

| Compounds of the formula II; $R^1$ = methyl in trans,trans-position to the N atom | | | |
|---|---|---|---|
| $R^2$ | $R^3$ | b.p. (°C.)/mbar | $n_D^{20}$ |
| H | CH(CH$_3$)$_2$ | 93–95/19 | 1.452 |
| H | C(CH$_3$)$_3$ | 94–97/14 | |

TABLE 1-continued

Compounds of the formula II; $R^1$ = methyl in trans,trans-position to the N atom

| $R^2$ | $R^3$ | b.p. (°C.)/mbar | $n_D^{20}$ |
|---|---|---|---|
| CH3 | CH3 | 82–84/18 | |
| H | CH=CH2 | 77–82/14 | 1.4627 |
| H | C(CH3)=CH2 | 96–99/16 | 1.4656 |
| H | CH=CH(CH3) | | |
| H | C≡CH | 93–96/18 | 1.472 |
| CH3 | C≡CH | | |
| H | CH2OCH3 | 117–120/20 | |
| H | CH2OC2H5 | | |
| CH3 | CH2OCH3 | 117–118/22 | |
| CH3 | CH2OC2H5 | | |
| H | CO2CH3 | 132–134/28 | |
| H | CO2C2H5 | 124–126/12 | 1.4586 |
| CH3 | CO2CH3 | 84–91/0.4 | 1.4683 |
| H | α-Furyl | 82–83/0.2 | |
| H | α-Tetrahydrofuryl | 144–147/18 | 1.4752 |
| H | CH(OCH3)2 | | |
| H | CH(OC2H5)2 | 146–149/24 | |
| CH3 | CH(OCH3)2 | | |
| H | CH(CH3)OCH3 | 110–112/24 | |
| H | C6H5 | oil | |

TABLE 2

Compounds of the formula II; $R^1$ = methyl in cis,trans-position to the N atom

| $R^2$ | $R^3$ | b.p. (°C.)/mbar | $n_D^{20}$ |
|---|---|---|---|
| H | CH(CH3)2 | | |
| H | C(CH3)3 | | |
| CH3 | CH3 | | |
| H | CH=CH2 | | |
| H | C(CH3)=CH2 | | |
| H | C=CH(CH3) | | |
| H | C≡CH | 96–99/22 | |
| CH3 | C≡CH | | |
| H | CH2OCH3 | | |
| H | CH2OC2H5 | | |
| CH3 | CH2OCH3 | | |
| CH3 | CH2OC2H5 | | |
| H | CO2CH3 | | |
| H | CO2C2H5 | 136–138/22 | |
| CH3 | CO2CH3 | | |
| H | α-Furyl | | |
| H | α-Tetrahydrofuryl | | |
| H | CH(OCH3)2 | | |
| H | CH(OC2H5)2 | | |
| CH3 | CH(OCH3)2 | | |
| H | CH(CH3)OCH3 | | |
| H | C6H5 | | |

TABLE 3

Compounds of the formula II; $R^1$ = methyl in cis,cis-position to the N atom

| $R^2$ | $R^3$ | b.p. (°C.)/mbar | $n_D^{20}$ |
|---|---|---|---|
| H | CH(CH3)2 | | |
| H | C(CH3)3 | | |
| CH3 | CH3 | | |
| H | CH=CH2 | | |
| H | C(CH3)=CH2 | | |
| H | C=CH(CH3) | | |
| H | C≡CH | 94–98/24 | |
| CH3 | C≡CH | | |
| H | CH2OCH3 | | |
| H | CH2OC2H5 | | |
| CH3 | CH2OCH3 | | |
| CH3 | CH2OC2H5 | | |
| H | CO2CH3 | | |
| H | CO2C2H5 | 134–136/20 | |
| CH3 | CO2CH3 | | |
| H | α-Furyl | | |
| H | α-Tetrahydrofuryl | | |
| H | CH(OCH3)2 | | |
| H | CH(OC2H5)2 | | |
| CH3 | CH(OCH3)2 | | |
| H | CH(CH3)OCH3 | | |

TABLE 3-continued

Compounds of the formula II; $R^1$ = methyl in cis,cis-position to the N atom

| $R^2$ | $R^3$ | b.p. (°C.)/mbar | $n_D^{20}$ |
|---|---|---|---|
| H | C6H5 | | |

TABLE 4

2,6-Dialkylcyclohexylformimines of the formula

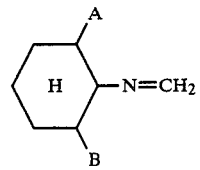

| A | B | b.p. (°C.)/mbar | $n_D^{20}$ |
|---|---|---|---|
| cis-CH3 | cis-CH3 | 57–59/20 | 1.4605 |
| cis-CH3 | trans-CH3 | 62–64/22 | 1.4618 |
| trans-CH3 | trans-CH3 | 59–60/20 | 1.4638 |
| cis-C2H5 | cis-C2H5 | 92–94/20 | |
| cis-C2H5 | trans-C2H5 | 110/40 | |
| trans-C2H5 | trans-C2H5 | | |

The compounds listed in the following tables may be, or were prepared analogously to Examples 1(b), 2(b) and 3(b):

TABLE 5

Compounds of the formula I; $R^1$ = methyl in trans,trans-position to the N atom

| No. | $R^2$ | $R^3$ | b.p.; $n_D^{20}$; m.p. |
|---|---|---|---|
| 4 | H | CH3 | |
| 5 | CH3 | CH3 | 70–74 |
| 6 | H | CH(CH3)2 | 52–53 |
| 7 | H | C(CH3)3 | 57–61 |
| 8 | CH3 | C2H5 | |
| 9 | H | CH=CH2 | 125/0.3 |
| 10 | CH3 | CH=CH2 | |
| 11 | H | (C(CH3)=CH2 | 130–132/0.5 |
| 12 | H | CH=CH(CH3) | |
| 13 | H | CH2C≡CH | |
| 14 | CH3 | C≡CH | |
| 15 | H | C≡C—CH3 | |
| 16 | H | CH2OCH3 | 140–145/0.2 |
| 17 | H | CH2OC2H5 | |
| 18 | H | CH2OnC3H7 | |
| 19 | CH3 | CH2OCH3 | 123–125 |
| 20 | CH3 | CH2OC2H5 | |
| 21 | H | CO2CH3 | 164–166/0.5 |
| 22 | CH3 | CO2CH3 | 165–170/0.4 |
| 23 | H | CO2C2H5 | 75–77 |
| 24 | H | CO2nC3H7 | |
| 25 | H | CO2iC3H7 | |
| 26 | H | α-Furyl | 165–166/0.7; 1.5712 |
| 27 | H | α-Furyl | |
| 28 | | | |
| 29 | H | α-Tetrahydrofuryl | 166–168/0.4 |
| 30 | CH3 | α-Furyl | |
| 31 | H | CH(OCH3)2 | |
| 32 | H | CH(OC2H5)2 | |
| 33 | CH3 | CH(OCH3)2 | |
| 34 | H | 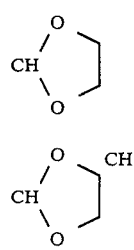 | |
| 35 | H | | |

TABLE 5-continued

Compounds of the formula I; $R^1$ = methyl in trans,trans-position to the N atom

| No. | $R^2$ | $R^3$ | b.p.; $n_D^{20}$; m.p. |
|---|---|---|---|
| 36 | H | —CH(O—CH₂—CH₂—O)—C₂H₅ (1,3-dioxolane) | |
| 37 | CH₃ | —CH(O—CH₂—CH₂—O)— (1,3-dioxolane) | |
| 38 | H | OCH₃ | 121–123/0.4 |
| 39 | H | OnC₅H₁₁ | |
| 40 | H | OnC₃H₇ | 135/0.05 |
| 41 | H | OiC₃H₇ | 133–135/0.4 |
| 42 | H | OnC₄H₉ | 140–142/0.08 |
| 43 | H | Osec.C₄H₉ | 136–138/0.5; 1.4827 |
| 44 | H | OiC₄H₉ | 138–140/0.5; 1.481 |
| 45 | H | Otert.C₄H₉ | 102–103 |
| 46 | H | O—Cyclopentyl | 40–42 |
| 47 | H | O—Cyclohexyl | |
| 48 | H | O—CH₂—cyclopropyl | 148–150; 1.4956 |
| 49 | H | O—CH₂—cyclopentyl | |
| 50 | H | OCH₂CH=CH₂ | 135–137/0.5; 1.4955 |
| 51 | H | OCH₂C(CH₃)=CH₂ | 135/0.5; 1.495 |
| 52 | H | OCH₂CH=C(CH₃)₂ | 160–163/0.4 |
| 53 | H | OCH₂C≡CH | 145–147/0.4; 1.502 |
| 54 | H | OCH₂C≡C—CH₃ | |
| 55 | H | O(CH₂)₂OCH₃ | 148–150/0.3 |
| 56 | H | O(CH₂)₂OC₂H₅ | 150–152/0.3 |
| 57 | H | O(CH₂)₂OnC₃H₇ | 161–163/0.3 |
| 58 | H | O(CH₂)₂OnC₄H₉ | 168–170/0.2 |
| 59 | H | Pyrazole-1 | oil |
| 60 | H | 1,2,4-Triazol-1-yl | |
| 61 | H | CH(CH₃)OCH₃ | 146–148/0.3 |
| 62 | H | C₆H₅ | 175–178/0.2 |
| 63 | H | OCH₂-tetrahydrofuryl | 162/2.0 |

TABLE 6

Compounds of the formula I; $R^1$ = methyl in cis,trans-position to the N atom

| No. | $R^2$ | $R^3$ | b.p.; $n_D^{20}$; m.p. |
|---|---|---|---|
| 64 | H | CH₃ | |
| 65 | CH₃ | CH₃ | |
| 66 | H | CH(CH₃)₂ | |
| 67 | H | C(CH₃)₃ | |
| 68 | CH₃ | C₂H₅ | |
| 69 | H | CH=CH₂ | |
| 70 | CH₃ | CH=CH₂ | |
| 71 | H | (C(CH₃)=CH₂ | |
| 72 | H | CH=CH(CH₃) | |
| 73 | H | C≡CH | 143–145/0.7 |
| 74 | CH₃ | C≡CH | |
| 75 | H | C≡C—CH₃ | |
| 76 | H | CH₂OCH₃ | |
| 77 | H | CH₂OC₂H₅ | |
| 78 | H | CH₂OnC₃H₇ | |
| 79 | CH₃ | CH₂OCH₃ | |
| 80 | CH₃ | CH₂OC₂H₅ | |
| 81 | H | CO₂CH₃ | |
| 82 | CH₃ | CO₂CH₃ | |
| 83 | H | CO₂C₂H₅ | 160–162/0.3 |
| 84 | H | CO₂nC₃H₇ | |
| 85 | H | CO₂iC₃H₇ | |
| 86 | H | α-Furyl | |
| 87 | H | β-Furyl | |
| 88 | H | α-Tetrahydrofuryl | |
| 89 | CH₃ | α-Furyl | |
| 90 | H | CH(OCH₃)₂ | |
| 91 | H | CH(OC₂H₅)₂ | |
| 92 | CH₃ | CH(OCH₃)₂ | |
| 93 | H | —CH(O—CH₂—CH₂—O)— (1,3-dioxolane) | |
| 94 | H | —CH(O—CH₂—CH₂—O)—CH₃ | |
| 95 | H | —CH(O—CH₂—CH₂—O)—C₂H₅ | |
| 96 | CH₃ | —CH(O—CH₂—CH₂—O)— | |
| 97 | H | OCH₃ | 50–53 |
| 98 | H | OC₂H₅ | 63–65 |
| 99 | H | OnC₃H₇ | 140/0.5 |
| 100 | H | OiC₃H₇ | |
| 101 | H | OnC₄H₉ | |
| 102 | H | Osec.C₄H₉ | |
| 103 | H | OiC₄H₉ | |
| 104 | H | Otert.C₄H₉ | |
| 105 | H | O—Cyclopentyl | |
| 106 | H | O—Cyclohexyl | |
| 107 | H | OCH₂-cyclopropyl | |
| 108 | H | OCH₂-cyclopentyl | |
| 109 | H | OCH₂CH=CH₂ | |
| 110 | H | OCH₂C(CH₃)=CH₂ | |
| 111 | H | OCH₂CH=C(CH₃)₂ | |
| 112 | H | OCH₂C≡CH | |
| 113 | H | OCH₂C≡C—CH₃ | |
| 114 | H | O(CH₂)₂OCH₃ | |
| 115 | H | O(CH₂)₂OC₂H₅ | |
| 116 | H | O(CH₂)₂OnC₃H₇ | |
| 117 | H | O(CH₂)₂OnC₄H₉ | |
| 118 | H | Pyrazol-1-yl | oil |
| 119 | H | 1,2,4-Triazol-1-yl | 103–106 |

TABLE 6-continued

Compounds of the formula I; $R^1$ = methyl in cis,trans-position to the N atom

| No. | $R^2$ | $R^3$ | b.p.; $n_D^{20}$; m.p. |
|---|---|---|---|
| 120 | H | (CH(CH$_3$)OCH$_3$ | |
| 121 | H | C$_6$H$_5$ | |

TABLE 7

Compounds of the formula I; $R^1$ = methyl in cis,cis-position to the N atom

| No. | $R^2$ | $R^3$ | b.p.; $n_D^{20}$; m.p. |
|---|---|---|---|
| 122 | H | CH$_3$ | |
| 123 | CH$_3$ | CH$_3$ | |
| 124 | H | CH(CH$_3$)$_2$ | |
| 125 | H | C(CH$_3$)$_3$ | |
| 126 | CH$_3$ | C$_2$H$_5$ | |
| 127 | H | CH=CH$_2$ | |
| 128 | CH$_3$ | CH=CH$_2$ | |
| 129 | H | C(CH$_3$)=CH$_2$ | |
| 130 | H | CH=CH(CH$_3$) | |
| 131 | H | C≡CH | 142–146/0.5 |
| 132 | CH$_3$ | C≡CH | |
| 133 | H | C≡C—CH$_3$ | |
| 134 | H | CH$_2$OCH$_3$ | |
| 135 | H | CH$_2$OC$_2$H$_5$ | |
| 136 | H | CH$_2$OnC$_3$H$_7$ | |
| 137 | CH$_3$ | CH$_2$OCH$_3$ | |
| 138 | CH$_3$ | CH$_2$OC$_2$H$_5$ | |
| 139 | H | CO$_2$CH$_3$ | |
| 140 | CH$_3$ | CO$_2$CH$_3$ | |
| 141 | H | CO$_2$C$_2$H$_5$ | |
| 142 | H | CO$_2$nC$_3$H$_7$ | |
| 143 | H | CO$_2$iC$_3$H$_7$ | |
| 144 | H | α-Furyl | |
| 145 | | | |
| 146 | H | β-Furyl | |
| 147 | H | α-Tetrahydrofuryl | |
| 148 | CH$_3$ | α-Furyl | |
| 149 | H | CH(OCH$_3$)$_2$ | |
| 150 | H | CH(OC$_2$H$_5$)$_2$ | |
| 151 | CH$_3$ | CH(OCH$_3$)$_2$ | |
| 152 | H | 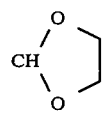 | |
| 153 | H | 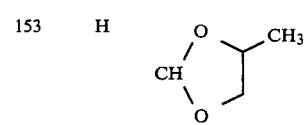 | |
| 154 | H | 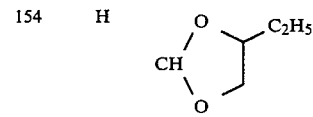 | |
| 155 | CH$_3$ | 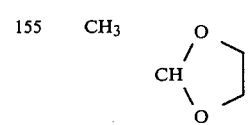 | |
| 156 | H | OCH$_3$ | 78–81 |
| 157 | H | OC$_2$H$_5$ | 126–128/0.4 |
| 158 | H | OnC$_3$H$_7$ | 133–135/0.4 |
| 159 | H | OiC$_3$H$_7$ | 130–132/0.5 |
| 160 | H | OnC$_4$H$_9$ | 140–143/0.3 |
| 161 | H | Osec.C$_4$H$_9$ | 137–139/0.5 |
| 162 | H | OiC$_4$H$_9$ | 138–140/0.5 |
| 163 | H | Otert.C$_4$H$_9$ | |
| 164 | H | O—Cyclopentyl | |
| 165 | H | O—Cyclohexyl | |

TABLE 7-continued

Compounds of the formula I; $R^1$ = methyl in cis,cis-position to the N atom

| No. | $R^2$ | $R^3$ | b.p.; $n_D^{20}$; m.p. |
|---|---|---|---|
| 166 | H |  | |
| 167 | H |  | |
| 168 | H | OCH$_2$CH=CH$_2$ | |
| 169 | H | OCH$_2$C(CH$_3$)=CH$_2$ | |
| 170 | H | OCH$_2$CH=C(CH$_3$)$_2$ | |
| 171 | H | OCH$_2$C≡CH | |
| 172 | H | OCH$_2$C≡C—CH$_3$ | |
| 173 | H | O(CH$_2$)$_2$OCH$_3$ | |
| 174 | H | O(CH$_2$)$_2$OC$_2$H$_5$ | |
| 175 | H | O(CH$_2$)$_2$OnC$_3$H$_7$ | |
| 176 | H | O(CH$_2$)$_2$OnC$_4$H$_9$ | |
| 177 | H | 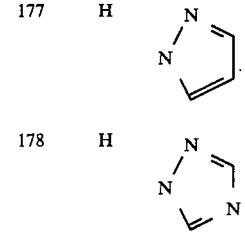 | |
| 178 | H |  | |
| 179 | H | CH(CH$_3$)OCH$_3$ | |
| 180 | H | C$_6$H$_5$ | |

TABLE 8

Compounds of the formula I; $R^1$ = ethyl in trans,trans-position to the N atom

| No. | $R^2$ | $R^3$ | b.p. $n_D^{20}$; m.p. |
|---|---|---|---|
| 181 | H | OCH$_3$ | 132/0.3 |
| 182 | H | OC$_2$H$_5$ | 146/0.6 |
| 183 | H | O—n-C$_3$H$_7$ | 154/0.5 |
| 184 | H | O—n-C$_4$H$_9$ | |
| 185 | H | O—i-C$_4$H$_9$ | |
| 186 | H | O—sec.-C$_4$H$_9$ | |

TABLE 9

Compounds of the formula I; $R^1$ = ethyl in cis,trans-position to the N atom

| No. | $R^2$ | $R^3$ | b.p.; $n_D^{20}$; m.p. |
|---|---|---|---|
| 187 | H | OCH$_3$ | 136–138/0.3 |
| 188 | H | OC$_2$H$_5$ | 138–140/0.2 |
| 189 | H | O—n-C$_3$H$_7$ | 148–150/0.2 |
| 190 | H | O—n-C$_4$H$_9$ | 160–162/0.5 |
| 191 | H | O—i-C$_4$H$_9$ | |
| 192 | H | O—sec.-C$_4$H$_9$ | |

TABLE 10

Compounds of the formula I; $R^1$ = ethyl in cis,cis-position to the N atom

| No. | $R^2$ | $R^3$ | b.p.; $n_D^{20}$; m.p. |
|---|---|---|---|
| 193 | H | OCH$_3$ | 54–56 |
| 194 | H | OC$_2$H$_5$ | 142–144/0.3; 1.4906 |
| 195 | H | O—n-C$_3$H$_7$ | 152–154/0.4; 1.4898 |
| 196 | H | O—n-C$_4$H$_9$ | 160–162/0.5; 1.4875 |
| 197 | H | O—i-C$_4$H$_9$ | |
| 198 | H | O-sec.-C$_4$H$_9$ | |

In particular, the novel active ingredients have a strong herbicidal action and are well tolerated by crop plants.

Application may be effected for instance in the form of directly sprayable solutions, powders, suspensions, dispersions, emulsions, oil dispersion, pastes, dusts, broadcasting agents, or granules by spraying, atomizing, dusting, broadcasting or watering. The form of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, and ground plastics.

Examples of formulations are given below:

I. 20 parts by weight of the compound of Example 39 is well mixed with 3 parts by weight of the sodium salt of diisobutyl-naphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By finely distributing the mixture in 20,000 parts by weight of water, a spray liquor is obtained containing 0.1% by weight of the active ingredient.

II. 3 parts by weight of the compound of Example 40 is intimately mixed with 97 parts by weight of particulate kaolin. A dust is obtained containing 3% by weight of the active ingredient.

III. 30 parts by weight of the compound of Example 41 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 42 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

V. 20 parts of the compound of Example 50 is intimately mixed with 2 parts of the calcium salt of dodecylbenzenesulfonic acid, 8 parts of a fatty alcohol polyglycol ether, 2 parts of the sodium salt of phenolsulfonic acid-urea-formaldehyde condensate and 68 parts of a paraffinic mineral oil. A stable oily dispersion is obtained.

VI. 90 parts by weight of the compound of Example 40 is mixed with 10 parts by weight of N-methyl-alpha-pyrrolidone. A mixture is obtained which is suitable for application in the form of very fine drops.

VII. 20 parts by weight of the compound of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 39 is dissolved in a mixture consisting of 40 parts by weight of cyclohexanone, 30 parts by weight of isobutanol, 20 parts by of the aduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

EXAMPLES DEMONSTRATING THE HERBICIDAL ACTION

The action of representatives of the novel compounds on the growth of unwanted and crop plants is demonstrated in greenhouse experiments described below:

The vessels employed for the experiments were plastic flowerpots having a volume of 300 cm$^3$, and which were filled with a sandy loam containing about 1.5% humus. In the case of soybeans, peat was added to ensure good growth. The seeds of the test plants were sown shallow, and separately, according to species.

The active ingredients were then immediately applied to the surface of the soil (=preemergence) as a suspension or emulsion in water by spraying through finely distributing nozzles. The amount of active ingredient applied in this treatment was equivalent to 1.0 kg/ha. The prior art compound used for comparison purposes was chloroacetic acid N-allyl-N-cyclohexylamide, which has already been mentioned.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

The pots were set up in the greenhouse—species from warmer areas at from 20° to 30° C., and species from moderate climates at 15° to 25° C. The experiments were run for from 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

In investigations into selective herbicidal action on preemergence application in the greenhouse, the compounds of Examples 3, 42 and 50, and of Examples 40, 41, 44 and 48 exhibited, at 1.0 kg/ha, a far better herbicidal action than the prior art comparative compound. At the same time, the first group of compounds was well tolerated by crop plants such as rape, soybeans and cotton, and the second group by rape and wheat.

In further experiments relating to selective herbicidal action on preemergence application in the greenhouse, the compounds of Examples 55, 56, 16, 23, 51 and 63 had a better herbicidal action on unwanted grasses (application rates varying from 0.5 to 2.0 kg/ha, depending on the active ingredient), without damaging broad-leaved crop plants such as sugarbeets, rape and cotton.

The compounds of Examples 157 and 158 also had a selective action in these crops on unwanted grasses.

Further biological tests revealed the control of unwanted grasses by preemergence application in the greenhouse of 0.5 and 2.0 kg/ha of compounds nos. 23 and 157 in soybeans.

Other greenhouse experiments also demonstrated that Setaria spp., for example, may be combated in wheat by preemergence application of 0.5 kg/ha of compounds nos. 55, 56 and 23.

The novel compounds are in particular effective against the following weeds:

| Botanical name | Common name |
| --- | --- |
| Amaranthus retroflexus | redroot pigweed |
| Digitaria sanguinalis | large crabgrass |
| Echinochloa crus-galli | barnyardgrass |
| Lolium multiflorum | Italian ryegrass |
| Matricaria spp. | chamomile species |
| Setaria spp. | foxtail species |

In the examples referred to here, the crop plants and unwanted plants were treated preemergence. However, the agents may also be applied when the crop plants are already established, but the weeds and grasses have not yet emerged or are in early growth stages (postemergence application).

If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants germinating and growing beneath the crop plants (post-directed, lay-by treatment).

In view of the good tolerance and the many application methods possible, the herbicides according to the invention may be used in a very wide range of crops for removing unwanted plants. The application rates may vary between 0.1 and 15 kg of active ingredient per hectare and more, depending on the type of soil and the object to be achieved.

The agents according to the invention may be used for instance in the following crops:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemon |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | parsley |

-continued

| Botanical name | Common name |
| --- | --- |
| Petroselinum crispum spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-alpha,alpha,beta,beta-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2-(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethyl-aniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline 3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate methyl N-3-(4'-fluorophenoxycarbonylamino)-phenylthiolcarbamate
methyl N-3-(2',4',5'-trimethylphenoxycarbonylamino)-phenylthiol-carbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
alpha,alpha-dichloropropionic acid, sodium salt
alpha,alpha-dichlorobutyric acid, sodium salt
alpha,apha,beta,beta-tetrafluoropropionic acid, sodium salt
alpha-methyl-alpha,beta-dichloropropionic acid, sodium salt
methyl alpha-chloro-beta-(4-chlorophenyl)-propionate
methyl alpha,beta-dichloro-beta-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(methylpropyn-2-yl)-2-chloroacetamide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide 2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide
2-(2-methyl-4-chlorophenoxy)-N-methoxyacetamide
2-(alpha-naphthoxy)-N,N-diethylpropionamide
2,2-diphenyl-N,N-dimethylacetamide
alpha-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(alpha,alpha-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(alpha,alpha,beta-beta-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea imidazolidin-2-one-1-carboxylic acid isobutylamide
1,2-dimethyl-3,5-diphenylpyrazolium-methylsulfate
1,2,4-trimethyl-3,5-diphenylpyrazlium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride 1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihyro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl alpha-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glucine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl-4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-alpha,alpha,beta-trifluoro-beta-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1-{4-[2-(4-methylphenyl)-ethoxy]-phenyl}-3-methyl-3-methoxyurea
2,6-dimethyl-N-(pyrazol-1-yl-methylenoxymethyl)-2-chloroacetanilide
2-methyl-6-ethyl-N-(pyrazol-1-yl-methylenoxymethyl)-2-chloroacetanilide
1-(alpha-2,4-dichlorphenoxypropionic acid)-3-(O-methylcarbamoyl)anilide
1-(alpha-2-bromo-4-chlorphenoxypropionic acid)-3-(O-methylcarbamoyl)-anilide
2-methyl-6-ethyl-N-(pyrazol-1-yl-ethylenoxymethyl)-2-chloroacetanilide
methyl-N-dichlorofluoromethylsulfenyl-[3-(N'-dichlorofluoro-methylsulfenyl-N'-phenylcarbamoyl-oxy)-phenyl]-carbamate
methyl-N-dichlorofluoromethylsulfenyl-[3-(N'-dichlorofluoromethylsulfenyl-N'-3-methylphenylcarbamoyl-oxy)-phenyl]-carbamate
N-(pyrazol-1-yl-methyl)-pyrazol-1-yl-acetic acid-2,6-dimethylanilide
N-(pyrazol-1-yl-methyl)-1,2,4-triazol-1-yl-acetic acid-2,6-dimethylanilide
2-(3'-trifluoromethylphenyl)-4H-3,1-benzoxazin-4-one
2-(2-thienyl)-4H-3,1-benzoxazin-4-one 2-(3-pentafluoroethoxyphenyl)-4H-3,1-benoxazin-4-one
2-(3-trifluoromethylthio-phenyl)-4H-3,1-benzoxazin-4-one
2-(3-difluorochloromethoxyphenyl)-4H-3,1-benzoxazin-4-one
5-nitro-2-(3-trifluoromethyl-phenyl)-4H-3,1-benzoxazin-4-one
5-chloro-2-(3-trifluoromethoxyphenyl)-4H-3,1-benzoxazin-4-one
5-chloro--[(3-alpha-alpha-beta-beta)-tetrafluoroethoxyphenyl]-4H-3,1-benzoxazin-4-one
5-fluoro-2-[(3-alpha-alpha-beta-beta)-tetrafluoroethoxyphenyl]-4H-3,1-benzoxazin-4-one
5-chloro-2-(4-difluorochloromethoxyphenyl)-4H-3,1benzoxazin-4-one
5-fluoro-2-(4-difluorochloromethoxyphenyl)-4H-3,1-benzoxazin-4-one
5-fluoro-2-(phenyl)-4H-3,1-benzoxazin-4-one
5-fluoro-2-(3-difluoromethoxyphenyl)-4H-3,1-benzoxazin-4-one
5-chloro-2-(phenyl)-4H-3,1-benzoxazin-4-one
3-(3,5-dichlorophenyl)-4-methoxycarbonyl-5-methylpyrazole
3-(3-chlorophenyl)-4-methoxycarbonyl-5-methylpyrazole
3-(3-fluorophenyl)-4-methoxycarbonyl-5-methylpyrazole
1-acetyl-3-(3-fluorophenyl)-4-methoxycarbonyl-5-methylpyrazole
1-acetyl-3-(3-chlorophenyl)-4-methoxycarbonyl-5-methylpyrazole
1-acetyl-3-(3-bromophenyl)-4-methoxycarbonyl-5-methylpyrazole
1-acetyl-3-(3,5-dichlorophenyl)-4-methoxycarbonyl-5-methylpyrazole
1-acetyl-3-thienyl-4-methoxycarbonyl-5-methylpyrazole
methyl N-3-chloro-4-isopropylphenyl-thiolcarbamate
methyl N-3-methyl-4-fluorophenyl-thiolcarbamate
methyl N-3-chloro-4-isopentylphenyl-thiolcarbamate
methyl N-3-chloro-4-difluoromethoxyphenyl-thiolcarbamate
methyl N-3-chloro-4-(1-chloroisopropyl)-phenyl-thiolcarbamate
1-(2-fluorophenyl)-3-methyl-5-iminoimidazolidin-2-one
1-(3-isopropylphenyl)-3-methyl-5-iminoimidazolidin-2-one
1-(4-isopropylphenyl)-3-methyl-5-iminoimidazolidin-2-one
1-[3-(1,1,2,2-tetrafluorethoxy)-phenyl]-3-methyl-5-iminoimidazolidin-2-one
1-(3,4-dichlorophenyl)-3-methyl-5-iminoimidazolidin-2-one
1-(3,4-difluorophenyl)-3-methyl-5-iminoimidazolidin-2-one
6-methyl-3-methoxy-5,6-dihydro-1,2,4,6-thiatriazin-5-one-1,1-dioxide
6-methyl-3-methoxy-5,6-dihydro-1,2,4,6-thiatriazin-5-one-1,1-dioxide, sodium salt
6-n-propyl-3-methoxy-5,6-dihydro-1,2,4,6-thiatriazin-5-one-1,1-dioxide
6-methyl-3-ethoxy-5,6-dihydro-1,2,4,6-thiatriazin-5-one-1,1-dioxide
6-n-propyl-3-ethoxy-5,6-dihydro-1,2,4,6-thiatriazin-5-one-1,1-dioxide, sodium salt
6-methyl-3-isopropoxy-5,6-dihydro-1,2,4,6-thiatriazin-5-one-1,1-dioxide
6-n-propyl-3-isopropoxy-5,6-dihydro-1,2,4,6-thiatriazin-5-one-1,1-dioxide
6-isopropyl-3-sec-butoxy-5,6-dihydro-1,2,4,6-thiatriazin-5-on-1,1-dioxide, sodium salt
N-3'-(2''-chloro-4''-trifluormethylphenoxy)-6'-nitrobenzoylanthranilic acid
methyl N-3'-(2''-chloro-4''-trifluoromethylphenxy)-6'-nitrobenzoylanthranilate
N-3'-(2''-chloro-4''-trifluormethylphenoxy)-6'-nitrobenzoylanthranilic acid, sodium salt
N-3'-(2''-chloro-4''-trifluoromethylphenoxy)-6'-nitrobenzoyl-3-chloroanthranilic acid
N-3'-(2''-chloro-4''-trifluoromethylphenoxy)-benzoyl-3-chloroanthranilic acid
N-3'-(2''-chloro-4''-trifluoromethylphenoxy)-benzoyl-3-methylanthranilic acid
N-3'-(2''-chloro-4''-trifluoromethylphenoxy)-benzoylanthranilic acid
N-3'-(2'',4''-dichlorophenoxy)-6'-nitrobenzoylanthranilic acid
N-[3'-(2''-chloro-4''-trifluoromethylphenoxy)-6'-nitrophenyl]-4H-1,3-benzoxazin-4-one
N-[3'-(2''-chloro-4''-trifluoromethylphenoxy)-6'-nitrophenyl]-4H-1,3-8-methoxybenzoxazin-4-one It may also be useful to apply the novel compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:
1. A chloroacetic acid cyclohexylamide of the formula

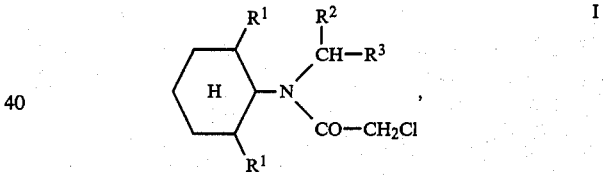

where $R^1$ is methyl, $R^2$ is hydrogen and $R^3$ is $C_1$–$C_8$-alkoxy, $C_3$–$C_6$-alkenyloxy, $C_3$–$C_6$-cycloalkylmethoxy, or $C_1$–$C_6$-alkoxyethoxy.

2. A compound of the formula I as set forth in claim 1, wherein the substituents $R^1$ are in cis-position to the nitrogen atom.

3. A compound of the formula I as set forth in claim 1, wherein the substituents $R^1$ are in trans-position to the nitrogen atom.

4. A compound of the formula I as set forth in claim 1, wherein the substituents $R^1$ are in cis,trans-position to the nitrogen atom.

5. A compound of the formula I of claim 1, wherein $R^3$ is $C_1$–$C_8$-alkoxy.

6. A herbicidal agent which comprises: a solid or liquid carrier and an effective amount of at least one compound of the formula I as set forth in claim 1.

7. A herbicidal agent which comprises a solid or liquid carrier and an effective amount of at least one compound of the formula I as set forth in claim 5.

8. A process for combating weeds, wherein an effective amount of at least one compound of the formula I as claimed in claim 1 is allowed to act on the weeds or areas threatened by them.

* * * * *